(12) United States Patent
Hwong

(10) Patent No.: US 11,339,858 B2
(45) Date of Patent: May 24, 2022

(54) ACTUATOR FOR A NEEDLE

(71) Applicant: Matthew Hwong, Fort McMurray (CA)

(72) Inventor: Matthew Hwong, Fort McMurray (CA)

( * ) Notice: Subject to any disclaimer, the term of this patent is extended or adjusted under 35 U.S.C. 154(b) by 24 days.

(21) Appl. No.: 16/290,220

(22) Filed: Mar. 1, 2019

(65) Prior Publication Data

US 2020/0232545 A1 Jul. 23, 2020

(30) Foreign Application Priority Data

Jan. 22, 2019 (CA) ................................ CA 3030899

(51) Int. Cl.
*F16H 23/02* (2006.01)
*F16H 23/10* (2006.01)
*A61M 37/00* (2006.01)

(52) U.S. Cl.
CPC ......... *F16H 23/02* (2013.01); *A61M 37/0076* (2013.01); *F16H 23/10* (2013.01)

(58) Field of Classification Search
CPC .......... F16H 23/00; F16H 23/02; F16H 23/10; A61M 37/0076
See application file for complete search history.

(56) References Cited

U.S. PATENT DOCUMENTS

| | | | | |
|---|---|---|---|---|
| 1,679,884 A | * | 8/1928 | Thomas | B23D 49/162 74/60 |
| 2,455,626 A | | 12/1948 | Traut | |
| 3,266,434 A | | 8/1966 | McAlvay | |
| 3,706,233 A | | 12/1972 | Sanz et al. | |
| 3,935,796 A | * | 2/1976 | Wood | F04B 1/2064 91/504 |
| 4,487,272 A | * | 12/1984 | Bleicher | B25D 11/062 173/205 |
| 5,279,552 A | * | 1/1994 | Magnet | A61M 37/0076 604/47 |
| 5,725,058 A | * | 3/1998 | Eriksson | B23D 51/16 30/392 |
| 7,134,508 B2 | | 11/2006 | Prell et al. | |
| 9,624,914 B2 | * | 4/2017 | Maruoka | F04B 1/2085 |
| 2001/0054352 A1 | * | 12/2001 | Sugiura | F04B 27/0886 92/61 |
| 2005/0010236 A1 | * | 1/2005 | Frister | A61M 37/0076 606/116 |
| 2008/0107369 A1 | * | 5/2008 | Fujita | F16C 33/32 384/463 |
| 2015/0066190 A1 | * | 3/2015 | Brown | B28B 11/12 700/160 |
| 2019/0113028 A1 | * | 4/2019 | Hemink | F04B 1/29 |

FOREIGN PATENT DOCUMENTS

GB 825229 12/1959

OTHER PUBLICATIONS

Downloaded from www.swashdrivetattoomachines.com: SWASHDRIVE—A History; Nov. 6, 2018; p. 1-4.

* cited by examiner

*Primary Examiner* — Prasad V Gokhale
(74) *Attorney, Agent, or Firm* — Pedersen and Company, PLLC; Ken J. Pedersen; Barbara S. Pedersen

(57) ABSTRACT

An actuator that can convert rotary motion into reciprocating motion. The actuator has a drive shaft and one or more ride plates mounted at an adjustable angle on the drive shaft. A reciprocating output element is coupled to the ride plates.

9 Claims, 4 Drawing Sheets

ACTUATOR FOR A NEEDLE

TECHNICAL FIELD

Actuators for needles.

BACKGROUND

In the art of controlled movement of needles, for example, in the tattoo art, there is a need for an actuator for a needle.

SUMMARY

There is disclosed a new rotary to linear actuator for a needle.

An actuator for converting rotary to linear motion, the actuator comprising a drive shaft mounted in a housing for rotation about an axis; a first ride plate mounted on the drive shaft to rotate with the drive shaft, the first ride plate being mounted at an adjustable angle between the first ride plate and the drive shaft; a reciprocating output element mounted on the housing and the reciprocating output element being coupled to the first ride plate; and the adjustable angle between the first ride plate and the drive shaft being adjustable by an adjustment member.

In various embodiments, there may be included any one or more of the following features: a second ride plate mounted on the drive shaft to rotate with the drive shaft to define an envelope between the first ride plate and second ride plate, the second ride plate being mounted at an adjustable angle between the second ride plate and the drive shaft; the reciprocating output element being coupled to the first ride place and the second ride plate by having a part located within the envelope; the adjustment member comprises a rod mounted to rotate with the drive shaft, the rod being movable axially in a direction parallel to the axis of the drive shaft, the rod being coupled to each of the first ride plate and the second ride plate; the adjustment member comprises a sleeve arrangement coupled to the rod to adjust axial movement of the rod, the sleeve arrangement comprises a first ring fixed to the housing with internal threads and a second ring with external threads within the first ring, and a third ride plate rotatable within the second ring, the third ride plate being fixed to the rod.

These and other aspects of the device and method are set out in the claims.

BRIEF DESCRIPTION OF THE FIGURES

Embodiments will now be described with reference to the figures, in which like reference characters denote like elements, by way of example, and in which:

FIG. 2 is shown partly in plan view and partly as a cross-section, hatching indicates a cross-section of the element.

DETAILED DESCRIPTION

Figure 1:
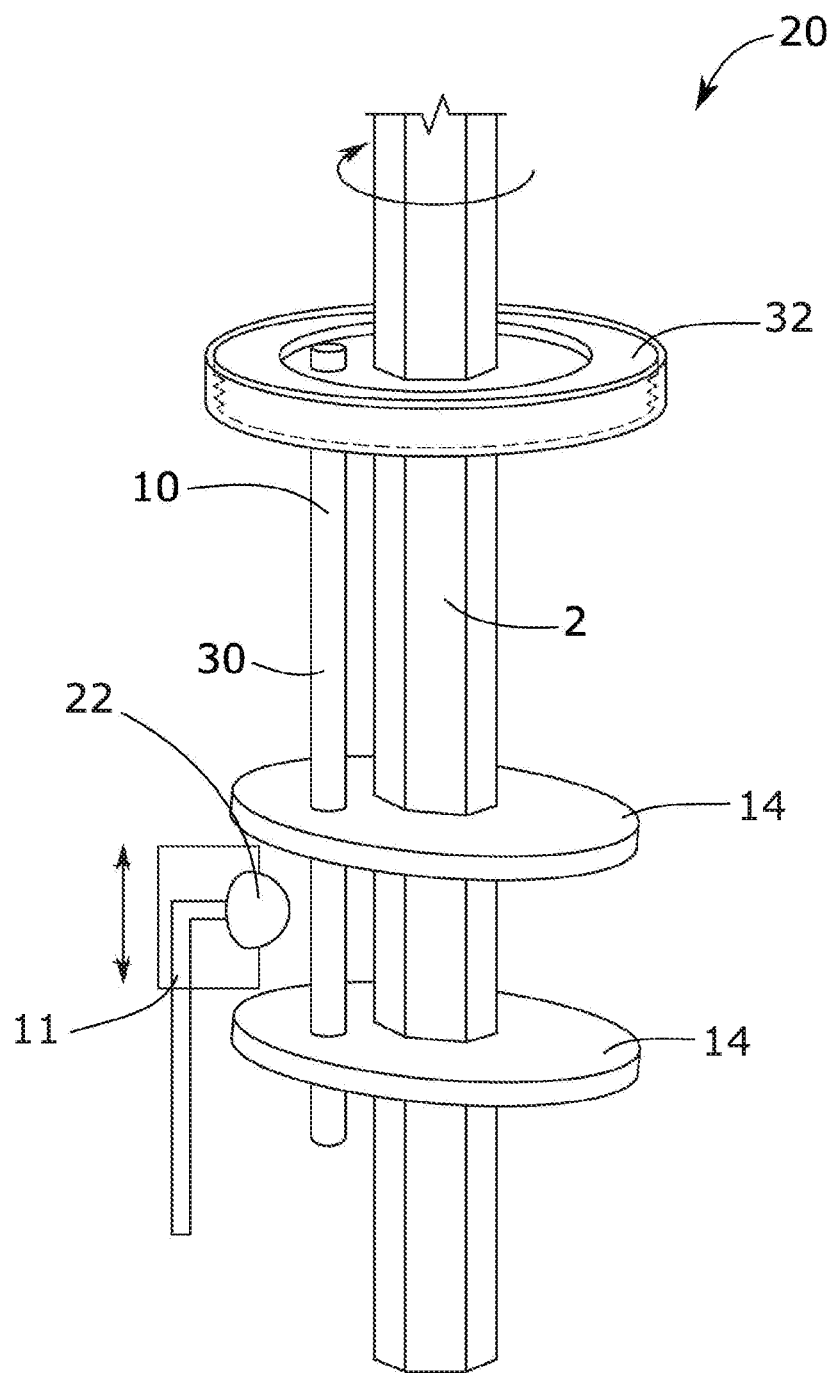
FIG. 1 is a basic schematic of an embodiment of an actuator.

FIG. 1 shows an embodiment of an actuator 20 that can efficiently convert rotary motion into reciprocating motion. The actuator may be in a tattoo machine. The actuator has an offset reciprocating output, which promotes good visibility of the user, and the ability to make vast changes to the throw of the reciprocating output in relation to the size of the unit.

Figure 2:
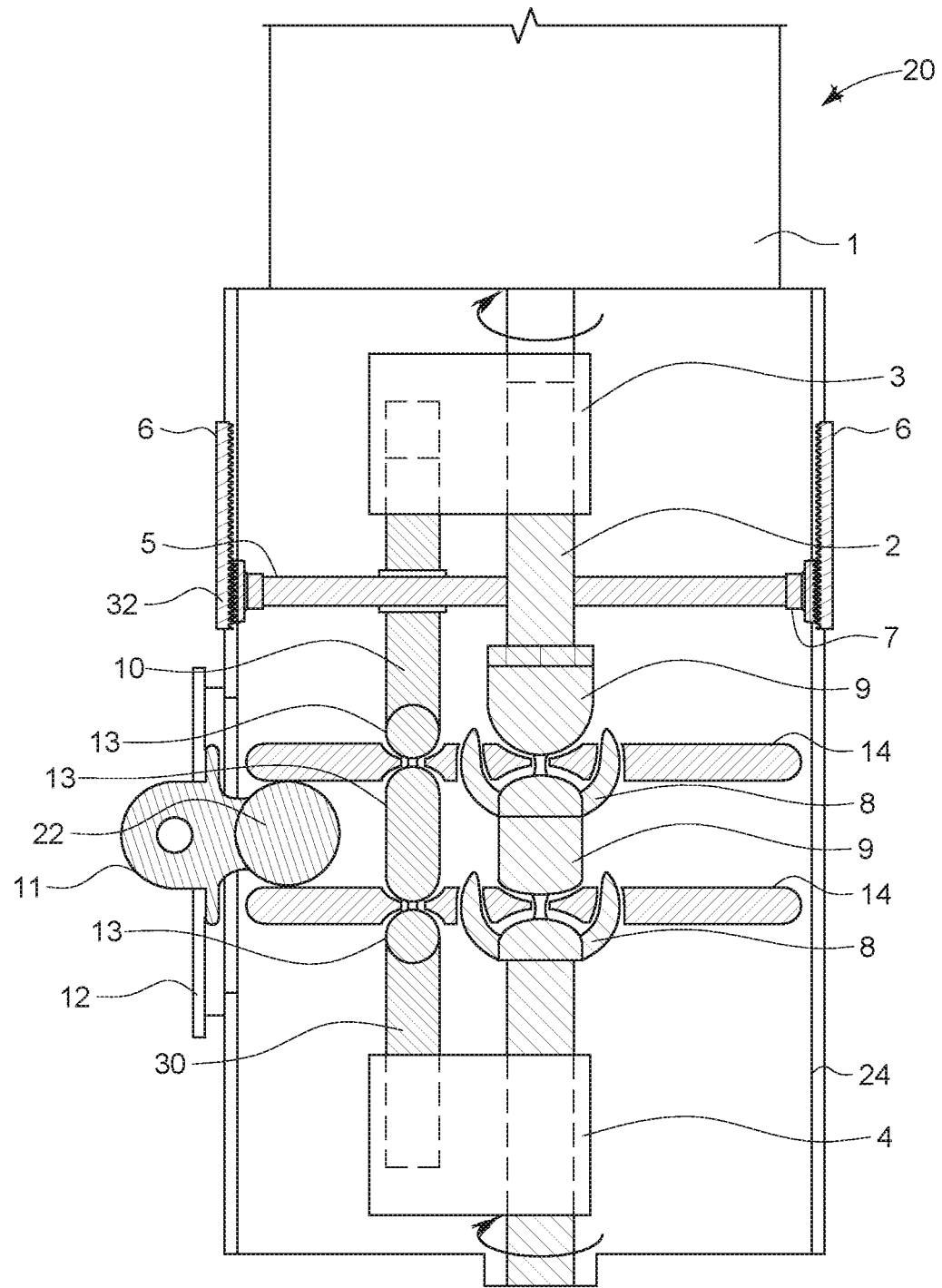
FIG. 2 is an exemplary embodiment of the actuator.

Referring to the exemplary embodiment shown in FIG. 2, reciprocal movement may be created in the reciprocating output 11 through the swashing action of ride plates 14. The reciprocating output 11 is mounted on a housing 24 of the machine and extends through a slot in the housing 24 to couple to the ride plates 14. For example, the reciprocating output 11 may comprise a guide 22 and may be coupled to a first and second ride plate 14 by the guide 22 located within a space or envelope between the first and second ride plates 14. The guide 22 is configured to mate the ride plates to the reciprocating output 11 through a range of angles. In operation, the guide 22 follows the vertical component of the swashing. The guide 22 may be a ball. An output slide retainer 12 may be provided on the housing 24 to constrain the movement of the reciprocating output 11 so the reciprocating output 11 cannot freely tilt. The output slide retainer 12 may be connected to the housing 24 by a flange.

The ride plates 14 are rotated by a drive shaft 2, described further below. The drive shaft is mounted in housing 24 for rotation about an axis. The ride plates 14 are mounted on the drive shaft and sit at an adjustable angle to the drive shaft 2. The ride plates are configured to be able to tilt between different angles to the drive shaft 2.

The angle of the ride plates to the drive shaft 2 may be adjusted by changing the axial position of the adjustment member 10. Adjustment member 10 may be movable axially in a direction parallel to the axis of the drive shaft and is coupled to the drive plates 14. Adjustment member 10 is mounted to rotate with the drive shaft. The adjustment member 10 may comprise a rod 30. The adjustment member 10 may comprise a freely rotating adjuster assembly to adjust the axial movement of the adjustment member 10. Adjuster assembly may comprise a sleeve arrangement 32 coupled to the rod 30 to adjust axial movement of the rod. The sleeve arrangement 32 may comprise a first ring 6 fixed to the housing with internal threads and a second ring 7 with external threads within the first ring, and a third ride plate 5 rotatable within the second ring, the third ride plate being fixed to the rod. The sleeve arrangement may be adjustable by twisting the first ring 6. While the ends of the adjustment member 10 may be free vertically, they are held in rotation to the drive shaft via a top shaft carrier 3 and a bottom shaft carrier 4. The adjustment member 10 will be inside both carriers 3,4 at any given time to varying depths, so that it is not subjected to undue twisting stresses.

The motor unit 1 is driven by a power cable (not shown) and rotates the drive shaft 2. The drive shaft 2 is splined at both ends to rotate the top shaft carrier 3 and the bottom shaft carrier 4. The shaft carriers 3, 4 are provided to carry the adjustment member 10 at the same revolution as the drive shaft.

Ride plates 14 may be driven and secured in any number of ways. The drive shaft 2 is configured to couple to the ride plates 14 to allow the ride plates to tilt freely while causing the ride plates 14 to rotate at the same revolutions as the drive shaft 2.

Drive shaft 2 extends through holes in the center of each ride plate 14. The diameter of the drive shaft may be smaller at the point where the drive shaft passes through each ride plate, or the diameter may be the same as the rest of the drive shaft. Drive shaft 2 may be threaded above the ride plates 14 to accommodate a disc retainer 9. Disc retainer 9 may be integral to drive shaft 2, or removably attached to drive shaft 2, for example by a threaded connection. Disc retainer 9 preferably has a larger diameter than the drive shaft 2 and is configured to keep the center of the ride plate 14 retained in same spot on the vertical axis while allowing the ride plate to tilt freely. One end of each ride plate 14 may be partially or fully convex.

The ride plates 14 are rotatingly connected to the drive shaft by a driving connection. The driving connection may be integral to the drive shaft or may be removably connected to the drive shaft. The driving connection may be some sort of ribbing or keying on the ride plates configured to engage with some sort of ribbing or keying on the drive shaft. As shown in FIG. 2, the driving connection may be wings 8 attached to the drive shaft below each of the ride plates 14, extending into or through complementary slots in the ride plates 14 to secure ride plates 14 and provide consistent power through a range of angles. There may be two or more wings. The wings may be on the drive shaft above the ride plates. If there are multiple ride plates, there may be an intermediate drive shaft section between the ride plates comprising a disc retainer above the lower drive plate and a driving connection below the upper drive plate. Alternatively, the driving connection may be gear teeth on the drive shaft mating to shaft gears with a convex face on the ride plates, to secure ride plates 14 and provide consistent power through a range of angles.

The ride plates 14 may have oblonged and concaved holes in their surfaces that allow the adjustment retainers 13 on adjustment member 10 to secure the adjustment height of the ride plates 14 at various tilt angles. The ends of the adjustment retainers 13 may be rounded to accommodate a tight fit. The adjustment retainers 13 may be integral to the adjustment member 10, or may be removably attached, for example threaded onto the adjustment member. The adjustment retainers 13 may be secured using other means, for example with clips.

Figure 3:
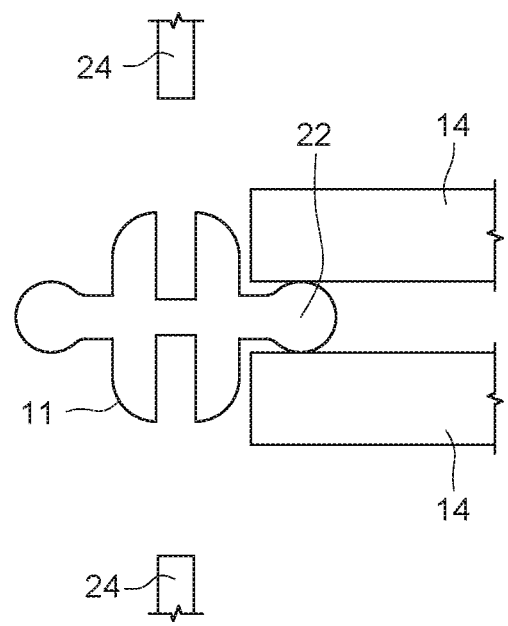
FIG. 3 shows a cross section of two ride plates at a first angle to the drive shaft.
Figure 4:
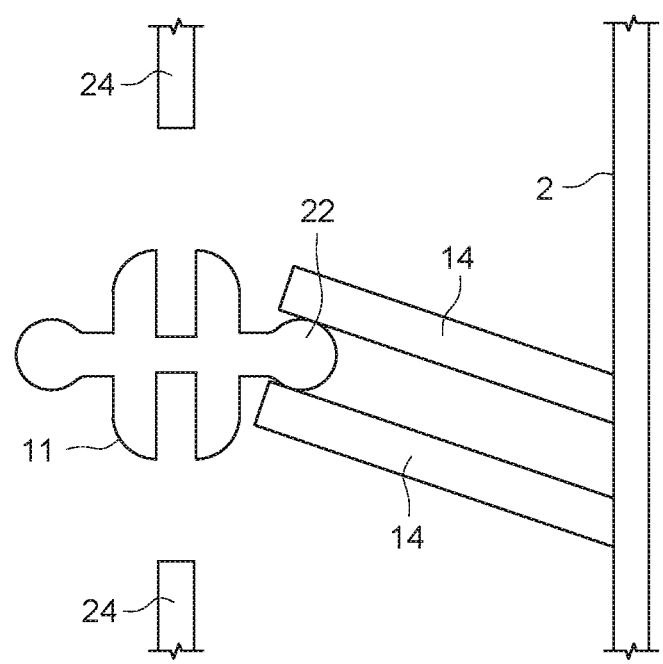
FIG. 4 shows a cross section of two ride plates at a second angle to the drive shaft.

FIGS. 3 and 4 show an example coupling of the ride plates 14 to the reciprocating output 11 while the ride plates are substantially perpendicular to the drive shaft (FIG. 3) and while the ride plates have been tilted to a different angle to the drive shaft (FIG. 4). The tilting action is provided via an adjustment member 10 which may lift and/or lower one end of the ride plates 14. In the case of a first and second ride plate 14, both ride plates may be moved by the adjustment member 10 simultaneously while the centers of the ride plates 14 are fixed in the vertical axis. In another embodiment, the driving connection may be a rounded wing, which may protrude into a slot inline with the angle shaft in the ride plate to drive it.

The ride plate 14 may be sandwiched between two rounded surfaces on the ends of the drive shaft which may be pressed onto, integral to, or threaded onto the drive shaft 2. The ride plate 14 may have a concave surface on both sides to accommodate the fit, while larger to accommodate for angle changes.

Figure 5:
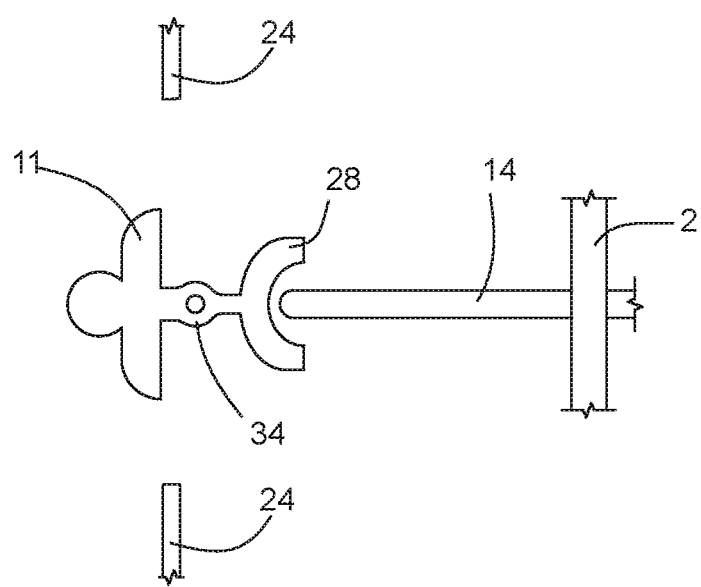
FIG. 5 shows a cross section of an embodiment of the actuator with one ride plate and a receptacle on the reciprocating output.
Figure 6:
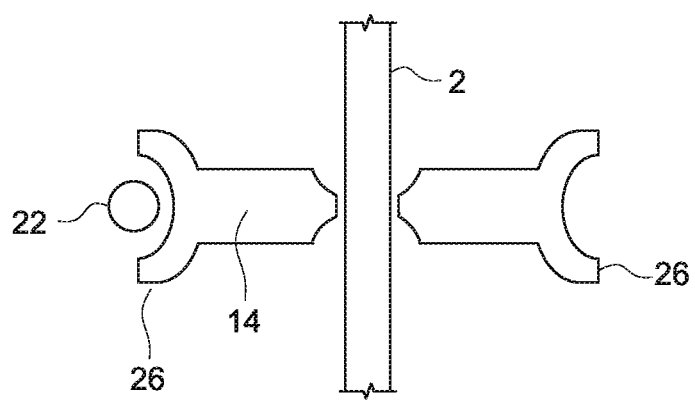
FIG. 6 shows a cross section of an exemplary embodiment of the actuator with one ride plate and a receptacle on the ride plate.

As shown in FIGS. 5 and 6, there may be only one ride plate on the drive shaft 2 and the reciprocating output 11 may be coupled to the ride plate 14. The ride plate may have an end that flares to form a receptacle 26, for example as shown in FIG. 6, which is sized to hold guide 22 of the reciprocating output 11. Alternatively the reciprocating output may have a receptacle 28 that the ride plates can slide in. In this embodiment reciprocating output 11 has a pivot 34 or gimbal and may have a telescoping stem to allow the receptacle to move up and down as the plate rotates, as shown in FIG. 5.

Any of the threaded connections may be associated with a detent so the threads do not vibrate down with use.

The length of the stroke of the reciprocating output may be adjustable. The stroke length depends on the thickness of ride plates 14, the diameter of the guide of the reciprocating output 11, and the angle the assembly is subjected to. The reciprocating output may further comprise a mechanism to increase the stroke length of the reciprocating output. For example, there may be a ring on the outside of the housing mounted to pivot as a lever.

The drive shaft may be driven by a motor at either end.

The reciprocating member 11 may connect for example to the needle of a tattoo machine.

Immaterial modifications may be made to the embodiments described here without departing from what is covered by the claims.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

Although this invention has been described above with reference to particular means, materials and embodiments, it is to be understood that the invention is not limited to these disclosed particulars, but extends instead to all equivalents within the scope of the following claims.

The invention claimed is:

1. An actuator for converting rotary to linear motion, the actuator comprising a drive shaft mounted in a housing for rotation about an axis;
   a first ride plate mounted on the drive shaft to rotate with the drive shaft, the first ride plate being mounted at an adjustable angle between the first ride plate and the drive shaft;
   a reciprocating output element mounted on the housing and the reciprocating output element being coupled to the first ride plate;
   the reciprocating output element extending from the first ride plate in a direction substantially perpendicular to a direction of the linear motion;
   the reciprocating output element extending beyond an exterior circumference of the first ride plate; and
   the adjustable angle between the first ride plate and the drive shaft being adjustable by an adjustment member, that comprises a rod mounted to rotate with the drive shaft, the rod being movable axially in a direction parallel to the axis of the drive shaft, the rod being coupled to the first ride plate.

2. The actuator of claim 1 further comprising:
   a second ride plate mounted on the drive shaft to rotate with the drive shaft to define an envelope between the first ride plate and second ride plate, the second ride plate being mounted at an adjustable angle between the second ride plate and the drive shaft; and
   the reciprocating output element being coupled to the first ride plate and the second ride plate by having a part located within the envelope.

3. The actuator of claim 2 in which the adjustment member comprises a rod mounted to rotate with the drive shaft, the rod being movable axially in a direction parallel to the axis of the drive shaft, the rod being coupled to each of the first ride plate and the second ride plate.

4. The actuator of claim 3 in which the adjustment member comprises a sleeve arrangement coupled to the rod to adjust axial movement of the rod.

5. The actuator of claim 4 in which the sleeve arrangement comprises a first ring fixed to the housing with internal threads and a second ring with external threads within the first ring, and a third ride plate rotatable within the second ring, the third ride plate being fixed to the rod.

6. The actuator of claim 1 in which the adjustment member comprises a sleeve arrangement coupled to the rod to adjust axial movement of the rod.

7. The actuator of claim 6 in which the sleeve arrangement comprises a first ring fixed to the housing with internal threads and a second ring with external threads within the first ring, and a third ride plate rotatable within the second ring, the third ride plate being fixed to the rod.

8. The actuator of claim 1 in which the reciprocating output element extends outside of the housing.

9. The actuator of claim 1 in which the reciprocating output element is coupled to the exterior circumference of the first ride plate.

\* \* \* \* \*